United States Patent
Davies

(10) Patent No.: US 9,061,049 B2
(45) Date of Patent: Jun. 23, 2015

(54) ANTIFUNGAL, ANTIBACTERIAL TOPICAL COMPOSITION FOR THE PREVENTION AND TREATMENT OF VARIOUS SKIN CONDITIONS INCLUDING DIAPER RASH

(71) Applicant: Matthew P Davies, Saint Johns, FL (US)

(72) Inventor: Matthew P Davies, Saint Johns, FL (US)

(\*) Notice: Subject to any disclaimer, the term of this patent is extended or adjusted under 35 U.S.C. 154(b) by 45 days.

(21) Appl. No.: 13/960,802

(22) Filed: Aug. 7, 2013

(65) Prior Publication Data

US 2015/0044309 A1  Feb. 12, 2015

(51) Int. Cl.
| | |
|---|---|
| *A01N 65/00* | (2009.01) |
| *A61K 36/752* | (2006.01) |
| *A61K 31/216* | (2006.01) |
| *A61K 31/22* | (2006.01) |
| *A61K 36/15* | (2006.01) |
| *A61K 36/185* | (2006.01) |
| *A61K 36/54* | (2006.01) |
| *A61K 36/61* | (2006.01) |

(52) U.S. Cl.
CPC ............. *A61K 36/752* (2013.01); *A61K 31/216* (2013.01); *A61K 31/22* (2013.01); *A61K 36/15* (2013.01); *A61K 36/185* (2013.01); *A61K 36/54* (2013.01); *A61K 36/61* (2013.01)

(58) Field of Classification Search
CPC ...... A61K 36/00; A61K 36/61; A61K 36/752
USPC .................................................. 424/725, 736
See application file for complete search history.

(56) References Cited

U.S. PATENT DOCUMENTS 7,060,306 B2 \*  6/2006  Springstead ................... 424/725

\* cited by examiner

*Primary Examiner* — Michael Meller
(74) *Attorney, Agent, or Firm* — Matthew P. Davies

(57) ABSTRACT

A topical, over the counter, all natural, organic, antifungal, antibacterial cream having superior moisturizing and water repellency performance that absorbs into the epidermis without spreading thereby eliminating and preventing the growth of the rash-causing fungus that causes diaper rash, and other skin irritation rashes.

1 Claim, No Drawings

ANTIFUNGAL, ANTIBACTERIAL TOPICAL COMPOSITION FOR THE PREVENTION AND TREATMENT OF VARIOUS SKIN CONDITIONS INCLUDING DIAPER RASH

CROSS-REFERENCES

None

GOVERNMENT RIGHTS

None

OTHER PUBLICATIONS

None

BACKGROUND OF INVENTION

1. Field of Invention

This invention relates generally to natural, organic, antifungal, and antibacterial topical cream formulations having superior moisturizing and water repellency performance for the prevention and elimination of common and sever diaper rash.

2. Discussion (Background of the Invention)

Historically diaper rash is believed to be a reaction of excrement, both solid and liquid, with the skin, causing irritation. Further, it is accepted within the industry that the rash causing agents in said excrement are from the acidic discharge of feces and urine creating a chemical burn that causes the skin to inflame. The counter to this acidic inflammation of the skin has been two fold. First, to create an impermeable barrier on the outer layer of the skin using petroleum based products such as petrolatum, and second, to employ amphoteric oxides that are insoluble in water but soluble in most acids thereby absorbing the acidic components and pulling them away from the skin.

One drawback to this petrolatum-amphoteric oxide approach is the limited absorption of the composition into the skin. Due to the high viscosity and highly mobile state of said compositions one finds that these compositions tend to spread throughout the region where diaper rash occurs rather than stay where (in the location) they were applied thereby spreading feces and urine along with it. Further these petroleum based products have limited, if any, absorption into the skin leaving a greasy residue to clean up after defecation.

A second drawback to the petrolatum-amphoteric oxide approach is the issue of moisture in the diaper region and the incorporation of said amphoteric oxides such as titanium oxide ($TiO_2$) or zinc oxide (ZnO), both inorganic astringents at various concentrations ranging from 10 to 40%. While zinc oxide, titanium oxide, and other amphoteric astringents are soluble in acids, 95% of human urine is water. Due to this limited solubility, it is commonly accepted within the industry that simply increasing the amount of zinc oxide (for example) will supply enough oxide to absorb any and all acid generated. This approach in and of itself has a number of drawbacks, the first being the powderized nature of these oxides. In using such high concentrations, in some cases up to 40% by weight, the product leaves behind a chalky white film on the skin even after the product is removed. Further, with the availability of cheaper oxides, most of which are of a particle size of 100 nm or less (nano), using concentrations of up to 40% by weight can potentially cause inhalation issues.

In the case of sever diaper rash, when the typical astringent based methods fail a prescription such as a polyene antifungal medication (commonly known as Nystatin), or a miconazole nitrate blend, as in Vusion®, is employed which tend to be egregiously expensive and can be toxic. Such prescriptions in the U.S. can cost in excess of $200.00. This is certainly expensive for first world nations but unattainable by most second and third world nations that reside along the equator where the prevalence of these rashes is highest.

While a multitude of attempts to repel, inhibit, buffer, and/or neutralize the acidic environment of urine and feces have been made within the industry, none have addressed the flora contained in typical excrement. Babies, due to accelerated growth, urinate and defecate more frequently than do adults. It can be shown that infants from birth to about two months of age can urinate on average up to 12 times a day and 5 to 10 times a day, thereafter up to about age 2. Depending on the condition and severity thereof, it can further be shown that babies can defecate up to 8 times a day under sever abdominal distress conditions. Urine typically has a pH range of 4.6 to 8 and generally leaves the body containing numerous Gram negative bacteria that can release ammonia containing compounds upon the breakdown of Urea. Further, upon defecation infant feces carries with it a host of proteins, enzymes, ammonia, fatty acids, and intestinal bacteria and fungus.

Of the human gut flora there are approximately 1000 different species comprising bacteria, fungus, and protozoa. Said bacterial species include *Bacteroides, Clostridium, Fusobacterium, Eubacterium, Ruminococcus, Peptococcus, Peptostreptococcus*, and *Bifidobacterium*. It is estimated that about 99% of the bacteria living in the colon come from a mere 30 to 40 species and make up to 60% of the dry mass of feces. Of the fungi present, *Candida, Saccharomyces, Aspergillus*, and *Penicillium* are known.

The most common fungus excreted in feces is *Candida albicans* a commensal gut flora which comes from the upper or lower intestinal tract. Candida can be accompanied in babies with an infection of the mouth commonly referred to as thrush. Typical symptoms in the diaper region include a reddening of the infected area from the anus to the thighs, including the genitals, genital creases, and the abdomen. The rash typically begins with a softening and reddening of the tissue in the perineum region from a combination of bacteria, fungus, chemical irritation, and enzymatic degradation. Satellite pustules (small, raised, red circular areas), characteristic of *Candida albicans* infections, appear around the perimeter of the infected region. These satellite pustules are the defining difference between a *Candida* infection and a simple frictional rash whereas due to the overlapping of skin acting to protect the non exposed areas, said pustules are typically not present.

In the most severe cases of rash and contact dermatitis a prescription antifungal cream is often used. These prescriptions tend to be a topical corticosteroid preparation in the form of hydrocortisone, or a corticosteroid/antifungal combination such as hydrocortisone/miconazole. These prescriptions tend to be prohibitively expensive and not readily available over the counter.

Several solutions to these issues exist, however none claim to simultaneously solve all of these problems. What is needed is an over the counter, all natural, organic, antifungal, antibacterial cream having superior moisturizing and water repellency performance properties that absorb into the epidermis without spreading, thereby killing the rash causing fungus that causes diaper rash, and other skin irritation rashes. Further, none of the aforementioned compositions have demonstrated the ability to kill fungus or bacteria while creating an absorbed waterproof barrier to urine and feces.

Due to the superior water repellency, absorption into the skin, antibacterial and antifungal properties of the present formulation, a buffering, enzymatic inhibition, or a chelating system is not needed as the acid environment of urine and feces does not interact with the skin. Further because the formulation completely absorbs into the skin there is no messy, greasy white reside left on the skin to spread the feces nor is there a need to clean off said residue after defecation has occurred. Lastly, due to the antibacterial and antifungal nature of the formulation there is no need for artificial preservatives to insure freshness.

Therefore it is the object of this invention to solve one or more of these problems.

SUMMARY OF INVENTION

In accordance with the teachings of this invention as embodied and described herein, a novel, over-the-counter, natural, organic, antifungal, antibacterial topical composition and method of manufacture having superior moisturizing and water repellency performance properties that absorbs into the epidermis without spreading for the prevention and treatment of moderate to severe diaper and other skin irritation rashes is presented.

As such, it is an object of the invention to provide a novel topical composition and method of manufacture for the prevention and treatment of moderate to severe diaper rash.

It is another object of the invention to provide a novel composition and method of manufacture for the prevention and treatment of moderate to severe rash associated with friction.

It is a final object of the invention to provide the above objects in an all natural, non-prescription, organic formulation.

By utilizing the improved formulation provided herein, such a moisturizing diaper cream that would create an unparalleled water barrier on the skin, eliminate the fungus associated with common, moderate, and sever diaper rash, not cause chemical burning, and not compromise the safety properties of the overall composition, is presented to overcome the limitations of pre-existing rash creams and bring a level of relief not heretofore experienced within the industry.

DETAILED DESCRIPTION OF THE INVENTION

The present invention relates to a natural, organic, topical skin cream, ointment, lotion, foam, or spray for use in the prevention and treatment of diaper rash, dermatitis, and frictional rash. The present invention principally works through a combination of inhibiting skin contact with feces or urine, as well as a blend of essential oils and aliphatic esters that inhibit and kill the bacteria and fungus that cause these various epidermal ailments.

When topically applied the foregoing blend forms a waterproof barrier on the epidermis that soaks into the skin leaving little to no residue behind. This is achieved via a novel combination of natural ingredients that mimic the skins epidermal layer and allow transport of said blend in the lipid bilayer rather than simply coat the top outer most layer. By increasing the lipid transport ability of this formulation, said formulation acts as a carrier of essential oils into the skin that prevent the growth of and eliminate the bacteria and fungus that cause various epidermal maladies. With said maladies being moderate to severe diaper rash, dermatitis, and frictional rash. This is done by deliberate choice of essential oils and aliphatic esters thus creating a superior water proof barrier to traditional oil-in-water type emulsion creams obtained through the use of gums, quaternary, or cationic compounds. Because of the superior absorbency of the present formulation, said present formulation is not greasy when applied and does not discolor the epidermal layer. Further when the time comes to change the baby's diaper, the area can be cleaned with a minimal of wipes, and in the case of the present invention a single wipe will do.

As various natural oils and aliphatic esters have different intrinsic properties such as molecular weight, densities, boiling points, etc. . . . said natural oils and aliphatic esters tend to vary in their viscosity and, as such, may be used to vary the delivery form of the present composition from a cream, to a foam, spray, or lotion. Further the delivery mechanism of said formulation may be a wipe, a diaper, a spray from an aerosol or pump dispenser, a roll-on, a dabber, physically rubbed in by hand or the like. Examples of said natural oils, aliphatic esters, aliphatic fatty acids of esters, and astringents are as follows:

Natural oils include sweet orange oil (*Citrus sinensis*), pine needle oil (*Pinus ponderosa, Pinus resinosa, Pinus sylvestris, Pinus strobes, Pinus monticola, Pinus armandii, Abies concolor*), fir needle oil (*Abies balsamea, Abies fraseri, Pseudotsuga menziesii, Abies pinsapo, Abies sibirica*), jojoba oil (*Simmondsia chinensis*), avocado oil (*Persea americana*), tea tree oil (*Melaleuca alternifolia*), argan oil (*Argania spinosa* L.), garlic oil (*Allium sativum*), yucca root (*Yucca glauca, Yucca brevifolia,* and *Yucca guatemalensis*), cod liver oil (*Gadus morhua,* and *Gadus macrocephalus*), sweet almond oil (*Prunus amygdalus*), coconut oil (*Cocos nucifera*), grapeseed oil (*Vitis sylvestris*), emu oil (*Eremophila longifolia, Eremophila gilesii, Eremophila denticulata, Eremophila bowmanii, Eremophila alternifolia*), myrtle oil (*Melaleuca nesophila, Melaleuca teretifolia, Melaleuca fulgens, Melaleuca diosmatifolia*), and olive oil (*Olea europaea*).

Aliphatic esters of fatty acids may include palmitate, palmitoleate, hydroxypalmitate, triacontanyl palmitate, myricyl palmitate, cetyl palmitate, crotic acid, 4-hydroxycinnamic acid, methoxycinnamic acid, and ω-hydroxycarboxylic acids.

Aliphatic fatty acids may include stearic acid, palmitic acid, myristic acid, arachidic acid, lauric acid, oleic acid, palmitoleic acid, linoleic acid, and α-linolenic acid.

Astringents may be $ZnO$, $TiO_2$, alum, oatmeal, acacia, sage, yarrow, witch-hazel, bayberry, tannic acid, and gallic acid.

Another novel aspect of the present formulation is the lack of a white residue left on the skin from the various astringents. Typical creams and lotions depend on the astringents ability to absorb urine and remove it from the skin and as such use an inordinate amount of said material which leaves a milky white residue with every application.

The following examples further illustrate the composition of the invention, and method of manufacture. The examples are illustrative only, and are not intended to limit the scope of the invention in any respect.

Example I

| DIAPER RASH CREAM | |
|---|---|
| INGREDIENT | CONCENTRATION RANGE (Percent by weight) |
| Aliphatic Oils | 1-60% |
| Aliphatic Esters of Fatty acids | 1-30% |

-continued

DIAPER RASH CREAM

| INGREDIENT | CONCENTRATION RANGE (Percent by weight) |
|---|---|
| Aliphatic Fatty Acids | 1-30% |
| Fragrance | 1-10% |
| Astringent | 1-30% |

Example II

DIAPER RASH CREAM

| INGREDIENT | CONCENTRATION (Percent by weight) |
|---|---|
| A blend of sweet orange oil, pine needle oil, fir needle oil, jojoba oil, avocado oil, tea tree oil, argan oil, garlic oil, yucca root, cod liver oil, sweet almond oil, coconut oil, grapeseed oil, emu oil, myrtle oil, and olive oil | 30% |
| A blend of beeswax, carnauba wax, candelilla wax, ouricury wax, sugarcane wax, and retamo wax | 30% |
| A blend of cocoa butter, mango butter, avocado butter, shea butter, aloe butter, coffee bean butter, cupuacu butter, hemp seed butter, murumuru butter, and shealoe butter | 30% |
| Fragrance | 5% |
| Zinc Oxide | 5% |

Example III

FRICTIONAL RASH CREAM

| INGREDIENT | CONCENTRATION (Percent by weight) |
|---|---|
| A blend of sweet orange oil, pine needle oil, fir needle oil, jojoba oil, avocado oil, tea tree oil, argan oil, garlic oil, yucca root, cod liver oil, sweet almond oil, coconut oil, grapeseed oil, emu oil, myrtle oil, and olive oil | 40% |
| A blend of beeswax, carnauba wax, candelilla wax, ouricury wax, sugarcane wax, and retamo wax | 30% |
| A blend of cocoa butter, mango butter, avocado butter, shea butter, aloe butter, coffee bean butter, cupuacu butter, hemp seed butter, murumuru butter, and shealoe butter | 20% |
| Fragrance | 5% |
| Zinc Oxide | 5% |

In the present embodiment of the invention the topical composition formulation is prepared in the following manner. Referring to examples I, II, and III, a stainless steel conical tank of appropriate volume is charged with a blend of aliphatic waxes and heated to 80° C. Next a blend of aliphatic butters is added and stirred at about 10 to 30 RPM until said blend of waxes and butters are completely melted and homogeneously mixed. Once the wax-butter blend is melted and homogeneous, the aliphatic oils are added along with the fragrance and mixed until homogeneous.

The solution is then cooled to and maintained at or about 40°-60° C. while constantly being mixed at about 75 RPM. While cooing is occurring the astringent is added. Once the astringent is added, cooling is ceased and the resulting mix let come to room temperature with continuous mixing. Lastly, the cooled mix is homogenized to ensure proper packaging density and viscosity. Said viscosity may be in the range between 50,000 and 200,000 centipoise. With appropriate quality control (Q.C.) the batch is ready for packaging.

Example IV

DIAPER RASH LOTION

| INGREDIENT | CONCENTRATION (Percent by weight) |
|---|---|
| A blend of sweet orange oil, pine needle oil, fir needle oil, jojoba oil, avocado oil, tea tree oil, argan oil, garlic oil, yucca root, cod liver oil, sweet almond oil, coconut oil, grapeseed oil, emu oil, myrtle oil, and olive oil | 39% |
| A blend of beeswax, carnauba wax, candelilla wax, ouricury wax, sugarcane wax, and retamo wax | 30% |
| A blend of cocoa butter, mango butter, avocado butter, shea butter, aloe butter, coffee bean butter, cupuacu butter, hemp seed butter, murumuru butter, and shealoe butter | 25% |
| Fragrance | 1% |
| Zinc Oxide | 5% |

Typically lotions are not regarded as being good moisturizers, whereas creams are known for their excellent moisturizing properties. Within the current formulation a lotion with excellent moisturizing properties may be achieved with the proper selection of oils, waxes, and butters. In the present embodiment of the invention the topical composition formulation for a lotion is prepared in a similar manner as with the creams but with the variation in ingredients shown in example IV. Referring now to example IV, a stainless steel conical tank of appropriate volume is charged with a blend of aliphatic waxes and heated to 80° C. Next a blend of aliphatic butters is added and stirred at about 10 to 30 RPM until said blend of waxes and butters are completely melted and homogeneously mixed. Once the wax-butter blend is melted and homogeneous, the aliphatic oils are added along with the fragrance and mixed until homogeneous.

The solution is then cooled to and maintained at or about 40°-60° C. while constantly being mixed at about 75 RPM. While cooing is occurring the astringent is added. Once the astringent is added cooling is ceased and the resulting mix let come to room temperature with continuous mixing. Lastly, the cooled mix is homogenized to ensure proper packaging density and viscosity. Said viscosity may be in the range between 50,000 and 200,000 centipoise. With appropriate Q.C. the batch is ready for packaging.

The various embodiments of the present invention as shown in examples I-IV may be arranged, designed, and formulated in a wide variety of different configurations that fall within the scope of the present invention, and may be applied to any type of delivery system.

The foregoing discussion discloses and describes merely exemplary embodiments of the present invention. One skilled in the art will readily recognize from such discussion and from the accompanying claims, that various changes, modifications, adaptations, and variations can be made therein without departing from the spirit and scope of the invention as defined in the following claims.

The invention claimed is:
1. A topical composition formulation consisting essentially of:
- a.) a blend of sweet orange oil, pine needle oil, fir needle oil, jojoba oil, avocado oil, tea tree oil, and argan oil;
- b.) a blend of aliphatic esters of fatty acids in a concentration by weight of about 1 to 30%, selected from the group consisting of palmitate, palmitoleate, hydroxypalmitate, triacontanyl palmitate, myricyl palmitate, cetyl palmitate, crotic acid, 4-hydroxycinnamic acid, methoxycinnamic acid, and omega-hydroxycarboxylic acids;
- c.) a blend of aliphatic fatty acids in a concentration by weight of about 1 to 30%, selected from the group consisting of stearic acid, palmitic acid, myristic acid, arachidic acid, lauric acid, oleic acid, palmitoleic acid, linoleic acid, and alpha-linolenic acid;
- d.) a fragrance in a concentration by weight of about 1 to 10%;
- e.) an astringent in a concentration by weight of about 1 to 30% selected from the group consisting of ZnO, TiO2, and Alum; and
- wherein said fragrance is selected from the group consisting of fir needle oil, pine needle oil, lavender oil, sweet orange oil, gardenia oil, rose oil, calendula oil, honeysuckle oil, vanilla, and vanillin.

* * * * *